(12) United States Patent
O'Heeron

(10) Patent No.: US 6,960,164 B2
(45) Date of Patent: *Nov. 1, 2005

(54) OBTURATOR TIP FOR A TROCAR

(75) Inventor: Peter T. O'Heeron, Houston, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 163 days.

This patent is subject to a terminal disclaimer.

(21) Appl. No.: 10/632,671

(22) Filed: Aug. 1, 2003

(65) Prior Publication Data

US 2005/0033304 A1 Feb. 10, 2005

(51) Int. Cl.$^7$ .................................................. A61B 1/00
(52) U.S. Cl. ...................... 600/114; 606/185; 600/127; 600/129
(58) Field of Search ................ 604/506, 158, 604/164.01, 164.06, 264, 170.02, 274; 606/185; 600/114, 117, 127, 129

(56) References Cited

U.S. PATENT DOCUMENTS

| | | | |
|---|---|---|---|
| 5,342,315 A | 8/1994 | Rowe et al. | |
| 5,350,364 A | 9/1994 | Stephens et al. | |
| 5,350,393 A | 9/1994 | Yoon | |
| 5,385,553 A | 1/1995 | Hart et al. | |
| 5,405,328 A | 4/1995 | Vidal et al. | |
| 5,407,433 A | 4/1995 | Loomas | |
| 5,411,515 A | 5/1995 | Harber et al. | |
| 5,411,635 A | 5/1995 | Francis et al. | |
| 5,512,053 A | 4/1996 | Pearson et al. | |
| 5,538,509 A | 7/1996 | Dunlap et al. | |
| 5,549,564 A | 8/1996 | Yoon | |
| 5,551,947 A | 9/1996 | Kaali | |
| 5,554,137 A | 9/1996 | Young et al. | |
| 5,554,167 A | 9/1996 | Young et al. | |
| 5,569,289 A | 10/1996 | Yoon | |
| 5,584,850 A | 12/1996 | Hart et al. | |
| 5,591,190 A | 1/1997 | Yoon | |
| 5,607,440 A | 3/1997 | Danks et al. | |
| 5,609,604 A | 3/1997 | Schwemberger et al. | |
| 5,624,459 A | * 4/1997 | Kortenbach et al. | 606/185 |
| 5,628,732 A | 5/1997 | Antoon, Jr. et al. | |
| 5,645,076 A | 7/1997 | Yoon | |
| 5,645,556 A | 7/1997 | Yoon | |
| 5,669,885 A | 9/1997 | Smith | |
| 5,674,184 A | 10/1997 | Hassler, Jr. | |
| 5,674,237 A | 10/1997 | Ott | |
| 5,685,820 A | 11/1997 | Riek et al. | |
| 5,697,947 A | 12/1997 | Wolf et al. | |
| 5,720,761 A | 2/1998 | Kaali | |
| 5,752,938 A | 5/1998 | Flatland et al. | |
| 5,792,113 A | 8/1998 | Kramer et al. | |
| 5,797,944 A | 8/1998 | Nobles et al. | |
| 5,810,863 A | 9/1998 | Wolf et al. | |
| 5,827,228 A | 10/1998 | Rowe | |
| 5,989,224 A | 11/1999 | Exline et al. | |
| 6,099,544 A | 8/2000 | Wolf et al. | |
| 6,238,407 B1 | 5/2001 | Wolf et al. | |
| 6,280,417 B1 | 8/2001 | Heron et al. | |
| 6,340,358 B1 | 1/2002 | O'Heeron et al. | |
| 6,544,277 B1 | 4/2003 | O'Heeron | |
| 6,551,282 B1 | 4/2003 | Exline et al. | |
| 6,685,630 B2 | * 2/2004 | Sauer et al. | 600/114 |
| 6,783,516 B2 | 8/2004 | O'Heeron | |
| 6,830,578 B2 | * 12/2004 | O'Heeron et al. | 606/185 |

* cited by examiner

Primary Examiner—Beverly M. Flanagan
(74) Attorney, Agent, or Firm—Clarence E. Eriksen

(57) ABSTRACT

An obturator tip for a trocar is disclosed. The obturator comprises a shaft having a distal or penetration end for insertion into a patient and a handling or proximal end for gripping by a surgeon. The penetration end of the shaft comprises a tip having an upper flat face and a lower flat face which taper away from the shaft toward the distal end. The tip further comprises flat side faces which also taper or slope from the shaft toward the distal end. A glide tip has a rounded end and extends outwardly along the side faces.

1 Claim, 2 Drawing Sheets

OBTURATOR TIP FOR A TROCAR

BACKGROUND OF THE INVENTION

1. Field of the Invention

The present invention relates to surgical instruments known as trocars which are used in endoscopic surgery to penetrate an anatomical cavity of a patient to provide communication with the cavity during a surgical procedure. More particularly, the present invention relates to an improved tip for an obturator which is used in a trocar.

2. Description of the Prior Art

Endoscopic surgery is a significant method of performing surgical operations and has become the surgical procedure of choice due to its patient care advantages over "open surgery." A particular type of endoscopic surgery is laparoscopic surgery. A significant advantage of laparoscopic surgery over open surgery is the decreased post-operative recovery time. In most instances, a patient is able to leave the hospital within hours after laparoscopic surgery has been performed, whereas with open surgery, a patient requires several days of hospital care to recover. Additionally, laparoscopic surgery achieves decreased incidents of post-operative abdominal adhesions, decreased post-operative pain, and enhanced cosmetic results.

Conventionally, a laparoscopic surgical procedure begins with the insufflation of the abdominal cavity with carbon dioxide. The introduction of this gas into the abdominal cavity lifts the abdominal wall away from the internal viscera. The abdominal wall is then pierced or penetrated with a device known as a trocar. A trocar includes a housing assembly, a cannula assembly attached to the housing assembly to form a bore through the trocar, and a piercing element called an obturator. The obturator slides through an access port formed on the upper end of the housing assembly and through the bore of the trocar. After insertion of the trocar through the abdominal wall of the patient, the obturator is removed by the surgeon while leaving the cannula protruding through the abdominal wall. The cannula may be fixed in place by using a fascia device, and laparoscopic instruments can then be inserted through the cannula to view internal organs and to perform surgical procedures.

Traditionally, the piercing tip of the obturator of a trocar has employed a sharp cutting blade to assist the surgeon in penetrating the abdominal wall. These obturators with cutting tips cut the tissue and muscle of the patient when inserted into the patient, and recovery time from the trauma of this cutting of tissue and muscle is necessary. Moreover, since the cutting tips are sharp, costly safety shield mechanisms are employed in trocars which operate to cover the obturator tip a short time after the obturator passes through the abdominal wall of the patient.

Certain trocars, for example, as disclosed in U.S. Pat. No. 5,817,601 to Goodwin, and U.S. Pat. No. 5,591,192 to Privitera have employed a pair of blunt-edged blades or tissue separators which are located on the tip of the trocar to facilitate the penetration or dissection of tissue.

Both of the trocar assemblies disclosed in U.S. Pat. No. 5,817,061 to Goodwin and U.S. Pat. No. 5,591,192 to Privitera are manufactured and sold by Ethicon Endo-Surgery, Inc. It is believed that trocars as described in the '061 and '192 patents have encountered significant problems since the tip of the obturator may be prone to failure. In particular, the tip of the trocars disclosed in the '061 and '192 patents is believed to have experienced incidents of snapping off during the insertion of the trocar. This failure may be attributable to the blunt shape of the tip and the forces to which the tip is subjected upon insertion.

An improvement over trocar car assemblies of the '061 and '192 patents is disclosed in U.S. patent application Ser. No. 09/994,321 filed Nov. 26, 2001 and assigned to the assignee of the present application. While the obturator tip disclosed in the application is an improvement over the trocars of '061 and '192 patents, the trocar of the '321 application has the disadvantage of employing a piercing tip.

SUMMARY OF THE INVENTION

A obturator in accordance with the present invention comprises a shaft which slidably engages the axial bore defined by the cannula assembly of a trocar. The shaft has a distal end for insertion into a patient and a proximal end for gripping by a surgeon.

The distal end is rounded and this rounded end functions to divide tissue as opposed to cutting tissue. The distal end of the shaft of the obturator includes a tip having an upper face and a lower face which have flat and gently sloping bevels from the shaft portion toward the distal end to assist in the insertion. The distal end also includes two flat side faces interposed between the upper and lower flat faces. The side faces also slope from the shaft to the distal end. The distal end has a glide tip which is interposed between the upper and lower flat faces in a plane substantially equidistant between the upper and lower faces. The glide tip has a rounded tip and beveled portions which slope downward from the upper flat face and extend from the distal end of the obturator toward the proximal end of the obturator. The obturator tip described above and the remainder of the obturator may be fabricated as a one piece obturator. Alternatively, the tip may be fabricated as a replaceable tip.

DESCRIPTION OF SPECIFIC EMBODIMENT

Figure 1:
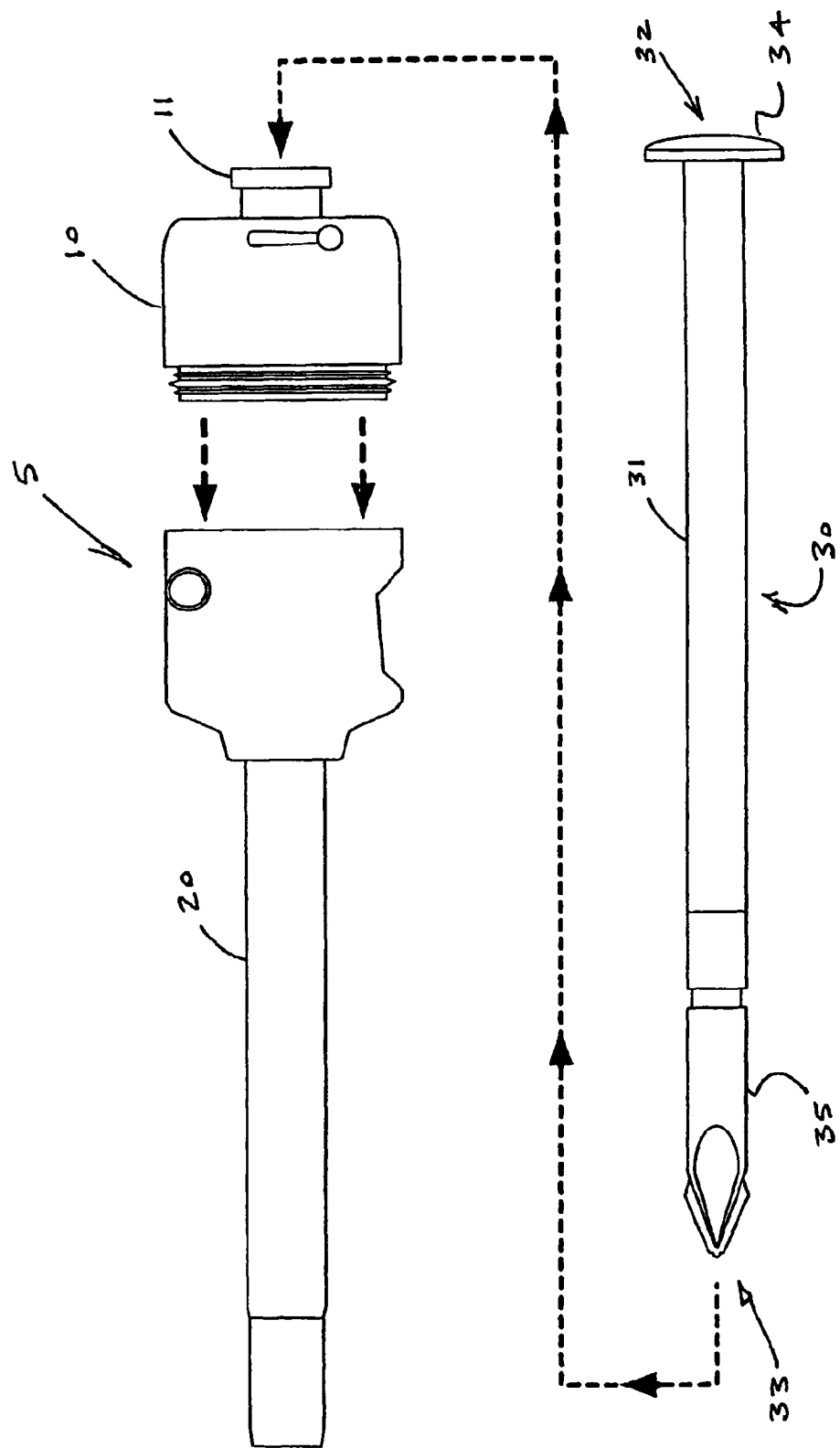
FIG. 1 is an exploded perspective view which illustrates components a trocar in which an obturator tip in accordance with the present invention may be used.

With reference to FIG. 1, a trocar 5 comprises a housing assembly 10 to which is attached a cannula assembly 20. The cannula assembly 20 is a hollow tube, and when attached to the housing assembly 10, a bore is defined through the trocar 5.

Still with reference to FIG. 1, trocar 5 also includes an obturator assembly 30 having a shaft 31 with a proximal or handling end 32 and a distal or penetrating end 33. An arcuate-shaped cap 34 is attached to the proximal or handling end 32 of the shaft 31 to facilitate insertion and manuevering of the obturator assembly 30 by a surgeon. At the distal end 33 of obturator 30 is a tip 35 which is used to penetrate a patient's body. The tip and the remainder of the obturator maybe formed such that the tip is removable or the tip and remainder of the obturator may be formed as a single unit. The obturator assembly 30 slides in the bore that is defined by the combination of housing assembly 10 and cannula assembly 20. Due to the construction of tip 35 as explained below, trocar 5 does not need a safety shield and the tip 35 may extend beyond the distal end of cannula 20.

While the shaft 31 of the obturator assembly 30 is preferably formed from a molded plastic material, those skilled in the art will appreciate that the obturator shaft may be formed from a variety of suitable materials.

Figure 2:
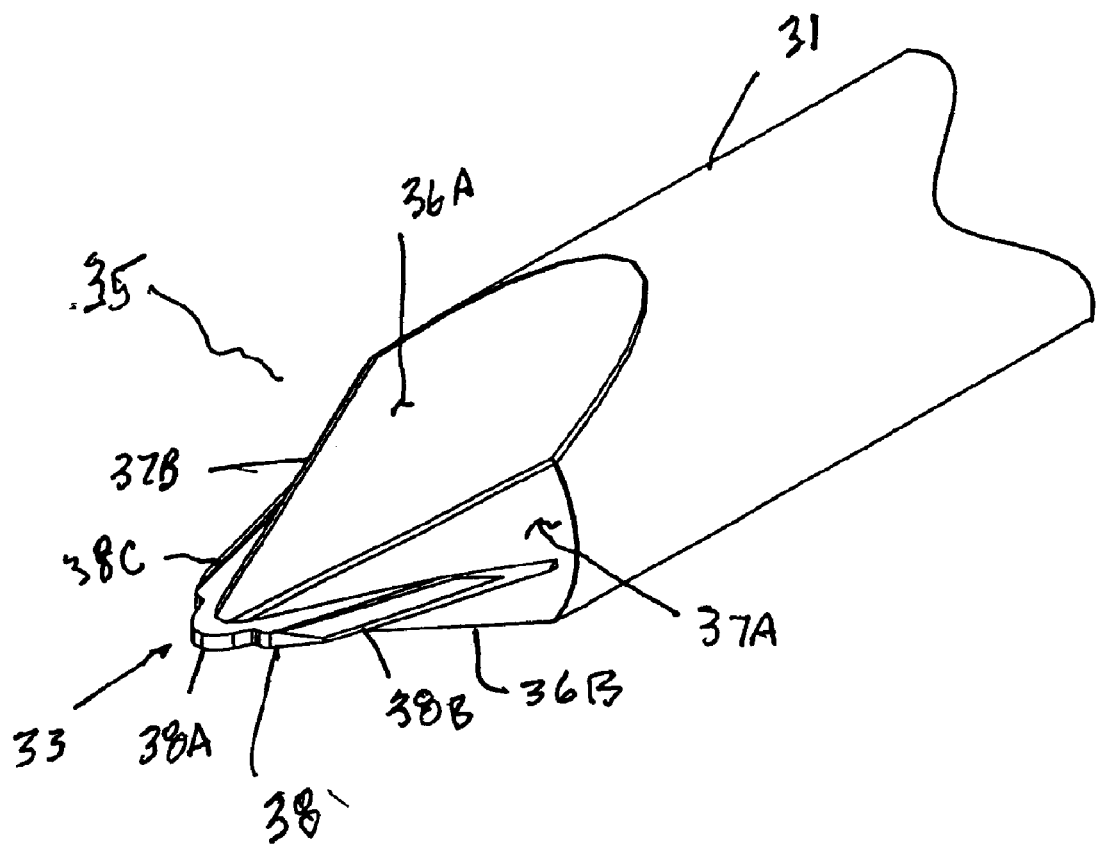
FIG. 2 is an enlarged perspective view of a tip of an obturator in accordance with the present invention.

With reference to FIG. 2, an obturator tip 35 in accordance with the present invention is shown. 1. Tip 35 comprises an upper face 36A and a lower face 36B. The upper face 36A and lower face 36B are flat and slope or taper away from the shaft 31 toward the distal end of the obturator. Tip 35 also comprises side faces 37A and 37B, which are flat and between upper and lower faces 36A and 36B. Side faces taper or slope away from shaft 31 toward the distal end 33.

A glide tip 38 extends outwardly from the side faces 37A and 37B is a plane substantially equidistant between the upper and lower faces 36A and 36B, respectively. The glide tip 38 also extends radially along the side faces as shown. The glide tip 38 has a rounded end 38A and beveled side portions 38B and 38C along the side faces. The beveled side portions 38B and 38C have bevels which extend downwardly from the upper face 36A.

The rounded end 38A of the obturator tip, as well as the glide bevel 38, function to divide tissue and muscle as opposed to cutting tissue and muscle. The upper and lower flat sloping faces 36A and 36B permit the tip 33 to be inserted into the patient relatively easily, and the bevels 38B and 38C on the tip glide 38 also aids in the insertion of the tip. The tip glide 38 has steps to divide tissue along one plane, while the upper and lower faces 36A and 36B dilate tissue in a plane perpendicular to the tip glide. The rounded end 38A of the tip glide 38 prevents injury to the patient when inserted in the patient.

An obturator having a tip in accordance with the present invention has a number of advantages over prior art obturators. It can be used on the initial penetration of the patient when the location of a vital obstruction may not be known and it eliminates cutting of tissue and muscle and the trauma and recovery resulting therefrom. No shielding mechanism is required with the obturator tip of the present invention, which results in reduced cost. An obturator tip in accordance with the present invention creates a smaller wound defect than a cutting blade, which results in quicker healing and better fascia fixation of the cannula. Finally, use of an obturator tip in accordance with the present invention results in dilation of the wound track instead of cutting the wound track, which reduces the risk of herniation.

What is claimed is:

1. A tip for an obturator which is used in a trocar, said obturator having a distal or penetration end, a proximal or handling end, and a shaft between the distal and proximal ends, said tip comprising:

(a.) upper and lower flat faces which slope from the shaft of the obturator toward the distal end of the obturator;

(b.) side faces which are flat, which are between the upper and lower flat faces, and which slope from the shaft toward the distal end of the obturator; and (c.) a glide tip which extends outwardly from the side faces in a plane substantially equidistant between the upper and lower faces and radially along the side faces, the glide tip having a rounded portion at the distal end of the obturator and a beveled portion along the side faces, the beveled portions having a downward bevel.

* * * * *